(12) United States Patent
Narasimhan et al.

(10) Patent No.: US 10,370,316 B2
(45) Date of Patent: *Aug. 6, 2019

(54) NARROW RANGE ALCOHOL ALKOXYLATES AND DERIVATIVES THEREOF

(71) Applicant: The Procter & Gamble Company, Cincinnati, OH (US)

(72) Inventors: Karunakaran Narasimhan, Mason, OH (US); Manuel G Venegas, West Chester, OH (US); Saurabh Mathur, Singapore (SG); Ralf Lange, Singapore (SG); Muhammad Sofian bin Asi Sihombing, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/139,144

(22) Filed: Sep. 24, 2018

(65) Prior Publication Data

US 2019/0023635 A1    Jan. 24, 2019

Related U.S. Application Data

(63) Continuation of application No. 15/791,522, filed on Oct. 24, 2017, now Pat. No. 10,099,983, which is a
(Continued)

(51) Int. Cl.
*C11D 3/34* (2006.01)
*C07C 43/13* (2006.01)
*C07C 43/11* (2006.01)
*C11D 1/66* (2006.01)
*C11D 3/20* (2006.01)
*C11D 1/29* (2006.01)
(Continued)

(52) U.S. Cl.
CPC .............. *C07C 43/13* (2013.01); *C07C 43/11* (2013.01); *C07C 43/135* (2013.01); *C11D 1/12* (2013.01); *C11D 1/29* (2013.01); *C11D 1/66* (2013.01); *C11D 1/721* (2013.01); *C11D 3/2068* (2013.01); *C11D 3/3409* (2013.01)

(58) Field of Classification Search
CPC .......... C11D 1/66; C07C 43/11; C07C 43/135
See application file for complete search history.

(56) References Cited

U.S. PATENT DOCUMENTS 4,223,163 A * 9/1980 Guilloty .................. C07C 41/03
510/356
4,265,790 A * 5/1981 Winston .................... C11D 3/08
510/324
(Continued)

FOREIGN PATENT DOCUMENTS

JP  2006-192375 A  7/2006
JP  2007-201435 A  2/2007

OTHER PUBLICATIONS

Matheson et al. (JAOCS, vol. 63, No. 3, Mar. 1986) (Year: 1986).*
(Continued)

*Primary Examiner* — Nicole M. Buie-Hatcher
*Assistant Examiner* — M. Reza Asdjodi
(74) *Attorney, Agent, or Firm* — Andres E. Velarde

(57) ABSTRACT

The present invention relates generally to narrow range alcohol alkoxylates and derivatives thereof, such as alkyl ether sulfates.

7 Claims, 2 Drawing Sheets

Related U.S. Application Data continuation of application No. 14/681,176, filed on Apr. 8, 2015, now Pat. No. 9,828,321.

(51) Int. Cl.
  *C11D 1/72* (2006.01)
  *C11D 1/12* (2006.01)

(56) References Cited

U.S. PATENT DOCUMENTS

| | | | |
|---|---|---|---|
| 4,441,881 A * | 4/1984 | Ruppert | C11D 1/72 427/393.4 |
| 4,540,828 A | 9/1985 | Yang | |
| 4,689,435 A * | 8/1987 | Edwards | C07C 41/03 560/263 |
| 5,417,878 A * | 5/1995 | Takahata | C11D 3/0084 510/108 |
| 6,593,287 B1 * | 7/2003 | Jordan, IV | A61K 8/39 510/221 |
| 6,846,791 B1 | 1/2005 | Dupont | |
| 7,576,244 B2 * | 8/2009 | Leeming | C07C 43/11 209/166 |
| 8,664,423 B2 | 3/2014 | Van Der Heijden et al. | |
| 8,889,900 B2 | 11/2014 | Kraus | |
| 9,828,321 B2 * | 11/2017 | Narasimhan | C07C 43/11 |
| 10,099,983 B2 * | 10/2018 | Narasimhan | C07C 43/11 |
| 10,099,984 B2 * | 10/2018 | Narasimhan | C07C 43/11 |
| 2002/0004953 A1 * | 1/2002 | Perry | C11D 3/162 8/142 |
| 2004/0266649 A1 * | 12/2004 | Thekkekandam | C11D 1/22 510/426 |
| 2005/0245772 A1 | 11/2005 | Fong et al. | |
| 2008/0051309 A1 | 2/2008 | Lin | |
| 2008/0064619 A1 | 3/2008 | Bastigkeit | |
| 2009/0144913 A1 * | 6/2009 | Yu | C11D 3/001 8/137 |
| 2011/0015110 A1 * | 1/2011 | Kellar | C11D 3/046 510/320 |
| 2011/0143986 A1 * | 6/2011 | Brooker | C11D 1/667 510/224 |
| 2012/0225943 A1 | 9/2012 | Gohl | |
| 2012/0288570 A1 * | 11/2012 | Zhu | D06L 4/12 424/616 |
| 2012/0291815 A1 | 11/2012 | Monsrud | |
| 2013/0313154 A1 * | 11/2013 | Hernandez | C11D 1/83 206/524.7 |
| 2014/0296127 A1 | 10/2014 | Hulskotter | |
| 2015/0264926 A1 * | 9/2015 | Boyd | A01N 37/36 514/557 |
| 2016/0297733 A1 * | 10/2016 | Narasimhan | C07C 43/11 |
| 2018/0044273 A1 | 2/2018 | Narasimhan et al. | |
| 2018/0044274 A1 | 2/2018 | Narasimhan et al. | |

OTHER PUBLICATIONS

K. Lee Matheson[a], Ted P. Matson[a] and Kang Yang[b,2], Peaked Distribution Ethoxylates—Their Preparation, Characterization and Performance Evaluation[1], Surfactants & Detergents Technical, JACOS, Mar. 1986, pp. 365-370.

Sasol, NOVEL® Narrow Range Ethoxylates, Advantages of NOVEL® Technology.

K.W.Dillan, Effects of the Ethylene Oxide Distribution on Nonionic Surfactant Properties, JAOCS, Jul. 1985, vol. 62 No. 7, pp. 1144-1151.

Cox M F: "Surfactants & Detergents the Effect of Peaking the Ethylene Oxidedistribution on the Performance of Alcohol Ethoxylates and Ether Sulfates"., Journal of the American Oil Chemists Society (JAOCS), Springer, DE, vol. 67, No. 9, Sep. 1, 1990 (Sep. 1, 1990), pp. 599-604. XP000882919, ISSN: 0003-021X, DOI: 10.1007/BF02540775.

Search Report for International Application No. PCT/US2016/026073, dated Jun. 13, 2016, containing 7 pages.

* cited by examiner

NARROW RANGE ALCOHOL ALKOXYLATES AND DERIVATIVES THEREOF

FIELD OF THE INVENTION

The present invention relates generally to narrow range alcohol alkoxylates and derivatives thereof, such as alkyl ethoxy sulfates.

BACKGROUND OF THE INVENTION

Alcohol alkoxylates and derivatives thereof, such as alkyl ethoxy sulfates (or alcohol ethoxy sulfates (AES)), find utility in a wide variety of applications, e.g., surfactants for use in detergents. The general reaction of alcohols and ethylene oxide to form ethoxylated alcohols or ethylene oxide adducts, has long been known and practiced on a commercial scale. For example, these ethylene oxide adducts have been used as detergents and cleaning agents, domestic and industrial laundry detergents, detergent builders, polishes, sanitizers, and dry cleaning materials.

Much literature is available in the general area of alkoxylation of alcohols. Many references are also available relating to the catalytic ability of various materials, and the mechanism and kinetics of these reactions. Generally, an alkoxylation reaction involving a compound having an active hydrogen, e.g., alcohol, is conducted by the condensation of an alkylene oxide using a suitable catalyst. Both basic, e.g., KOH, and acidic catalysts, e.g., $BF_3$, are known for use in alkoxylating alcohols. Alkoxylation of alcohols, however, produces a distribution of various adducts (homologs), not a pure compound. For example, in surfactant applications, an adduct with too few ethylene oxide molecules may not be effective because of poor solubility, while an adduct with too many ethylene oxide molecules may likewise be undesirable because surface tension reduction per unit mass decreases drastically with increasing molecular weight. Thus, there is a need for alkoxylates with a narrow distribution in the selected mole adduct range for the particular use of the material.

Known acid catalyzed reactions, such as $BF_3$, produce narrow range (peaked) alcohol alkoxylates, but these catalysts produce undesirable side products that must be separated and removed prior to use. Base catalysts normally do not produce the level of by-products which acidic catalysts do, but provide a much broader distribution of alkoxylation adducts. Therefore, it would be desirable to provide alcohol alkoxylates with a narrow distribution of the preferred mole adducts, which are produced by a catalyst system that does not produce undesirable by-products.

The use of a catalyst composition obtained by mixing a zinc salt of organosulfonic acid in one or more liquids selected from water, lower alcohols, higher alcohols, glycol ethers and aromatic solvents, where the ratio of organosulfonic acid/zinc oxide=5/1 to 1/10 (mole ratio), is known. However, the use of zinc organosulfonic acid as a catalyst involves another separate process to make the zinc salt of the organosulfonic acid.

SUMMARY OF THE INVENTION

The present disclosure attempts to solve one more of the needs by providing a composition comprising an alcohol ethoxylate of formula (I):

$$R\text{---}(OCH_2CH_2)_n\text{---}OH \quad (I)$$

where R is selected from a saturated or unsaturated, linear or branched, $C_8$-$C_{20}$ alkyl group, where $0 \leq n \leq 10$, and where the average value of n is about 1, where less than about 7% by weight of the alcohol ethoxylate are ethoxylates having $n \geq 3$ and less than about 35% by weight of the alcohol ethoxylate are ethoxylates having n=0.

The present disclosure further relates to a composition comprising an alcohol ethoxylate of formula (I):

$$R\text{---}(OCH_2CH_2)_n\text{---}OH \quad (I)$$

where R is selected from a saturated or unsaturated, linear or branched, $C_8$-$C_{20}$ alkyl group, where $0 \leq n \leq 10$, and where the average value of n is about 2, where from about 9% to about 13% by weight of the alcohol ethoxylate are ethoxylates having $n \geq 4$ and from about 9% to about 13% by weight of the alcohol ethoxylate are ethoxylates having n=0.

The present disclosure also relates to a composition comprising an alcohol ethoxylate of formula (I):

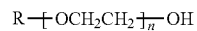

$$R\text{---}(OCH_2CH_2)_n\text{---}OH \quad (I)$$

where R is selected from a saturated or unsaturated, linear or branched, $C_8$-$C_{20}$ alkyl group, where $0 \leq n \leq 10$, and where the average value of n is about 3, where from about 1% to about 5% by weight of the alcohol ethoxylate are ethoxylates having n=0.

The present disclosure also relates to a composition comprising an alcohol ethoxylate of formula (I):

$$R\text{---}(OCH_2CH_2)_n\text{---}OH \quad (I)$$

wherein R is a $C_{14}$ or $C_{15}$ (or a mixture thereof) alkyl group, $0 \leq n \leq 10$, and the average value of n is about 2.5, wherein less than about 6% by weight of the alcohol ethoxylate are ethoxylates having $n \geq 6$ and less than about 6% by weight of the alcohol ethoxylate are ethoxylates having n=0.

The present disclosure also relates to sulfated derivatives of the alcohol ethoxylates described above.

The present disclosure further relates to a concentrated composition comprising from about 1% to about 10% by weight of the composition of a $C_{1-14}$ sulfonic acid, e.g., methane sulfonic acid, dodecylbenzene sulfonic acid, and from about 70% to about 99% by weight of a narrow range alcohol ethoxylate having an average degree of ethoxylation ranging from about 1 to about 10.

The present disclosure further relates to a concentrated composition comprising from about 1% to about 10% by weight of the composition of a $C_{1-14}$ sulfonic acid, e.g., methane sulfonic acid, dodecylbenzene sulfonic acid, and from about 10% to about 85% by weight of a narrow range alcohol ethoxy sulfate having an average degree of ethoxylation ranging from about 1 to about 10.

DETAILED DESCRIPTION OF THE INVENTION

Figure 1:
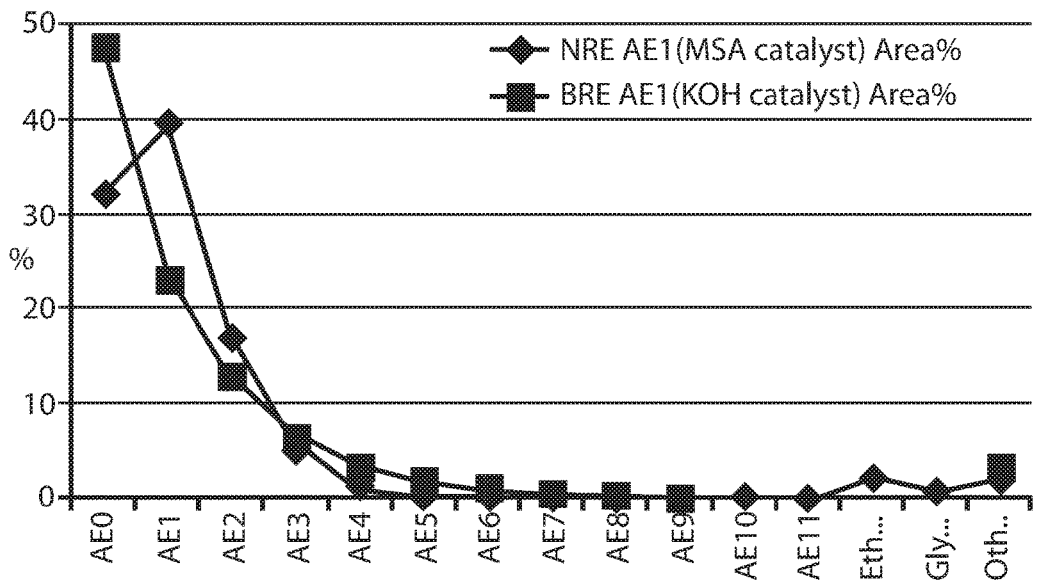
FIG. 1 illustrates the homolog distribution of ethoxylated $C_{12-14}$ alcohol prepared from the methane sulfonic acid (MSA)-catalyzed ethoxylation of the alcohol with 1 moles of ethylene oxide and the homolog distribution of ethoxylated $C_{12-14}$ alcohol prepared from the potassium hydroxide-catalyzed ethoxylation of the alcohol with 1 moles of ethylene oxide. The distribution is determined by GC.

Features and benefits of the present invention will become apparent from the following description, which includes examples intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein in reference to formula (I), the term "average value of n" refers to the average moles of ethylene oxide, which is the same as the average degree of ethoxylation. The average n may be an integer or a fraction.

As used herein, the articles including "the," "a" and "an" when used in a claim or in the specification, are understood to mean one or more of what is claimed or described.

As used herein, the terms "include," "includes" and "including" are meant to be non-limiting.

The term "substantially free of" or "substantially free from" as used herein refers to either the complete absence of an ingredient or a minimal amount thereof merely as impurity or unintended byproduct of another ingredient. A composition that is "substantially free" of/from a component means that the composition comprises less than about 0.5%, 0.25%, 0.1%, 0.05%, or 0.01%, or even 0%, by weight of the composition, of the component.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All cited patents and other documents are, in relevant part, incorporated by reference as if fully restated herein. The citation of any patent or other document is not an admission that the cited patent or other document is prior art with respect to the present invention.

In this description, all concentrations and ratios are on a weight basis of the detergent composition unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Narrow Range Alcohol Ethoxylate

The alcohol ethoxylates disclosed herein have the following general formula (I):

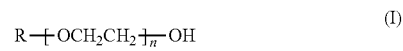

$$R\!-\!\!\left[\mathrm{OCH_2CH_2}\right]_{\overline{n}}\!-\!OH \qquad (I)$$

where R is selected from a saturated or unsaturated, linear or branched, $C_8$-$C_{20}$ alkyl group and where $0 \leq n \leq 10$.

The alcohol ethoxylates described herein are typically not single compounds as suggested by their general formula (I), but rather, they comprise a mixture of several homologs having varied polyalkylene oxide chain length and molecular weight. Among the homologs, those with the number of total alkylene oxide units per mole of alcohol closer to the most prevalent alkylene oxide adduct are desirable; homologs whose number of total alkylene oxide units is much lower or much higher than the most prevalent alkylene oxide adduct are less desirable. In other words, a "narrow range" or "peaked" alkoxylated alcohol composition is desirable. A "narrow range" or "peaked" alkoxylated alcohol composition refers to an alkoxylated alcohol composition having a narrow distribution of alkylene oxide addition moles.

Figure 2:
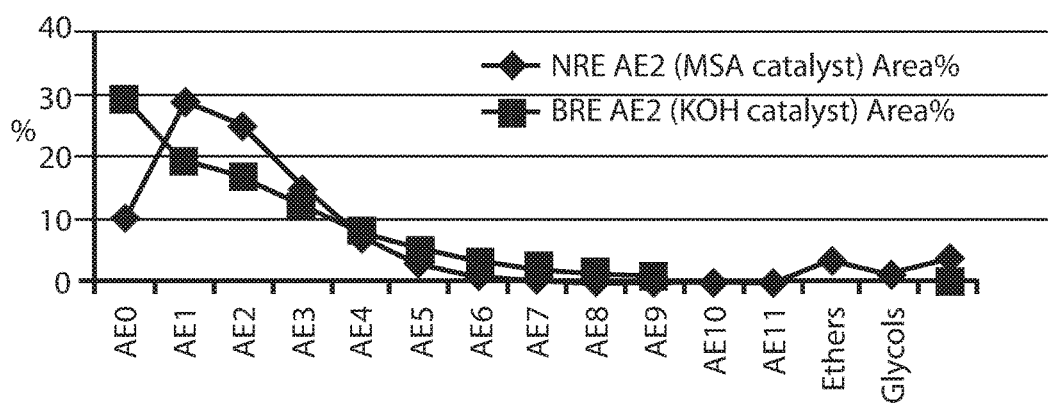
FIG. 2 illustrates the homolog distribution of ethoxylated $C_{12-14}$ alcohol prepared from the methane sulfonic acid (MSA)-catalyzed ethoxylation of the alcohol with 2 moles of ethylene oxide and the homolog distribution of ethoxylated $C_{12-14}$ alcohol prepared from the potassium hydroxide-catalyzed ethoxylation of the alcohol with 2 moles of ethylene oxide. The distribution is determined by GC.
Figure 3:
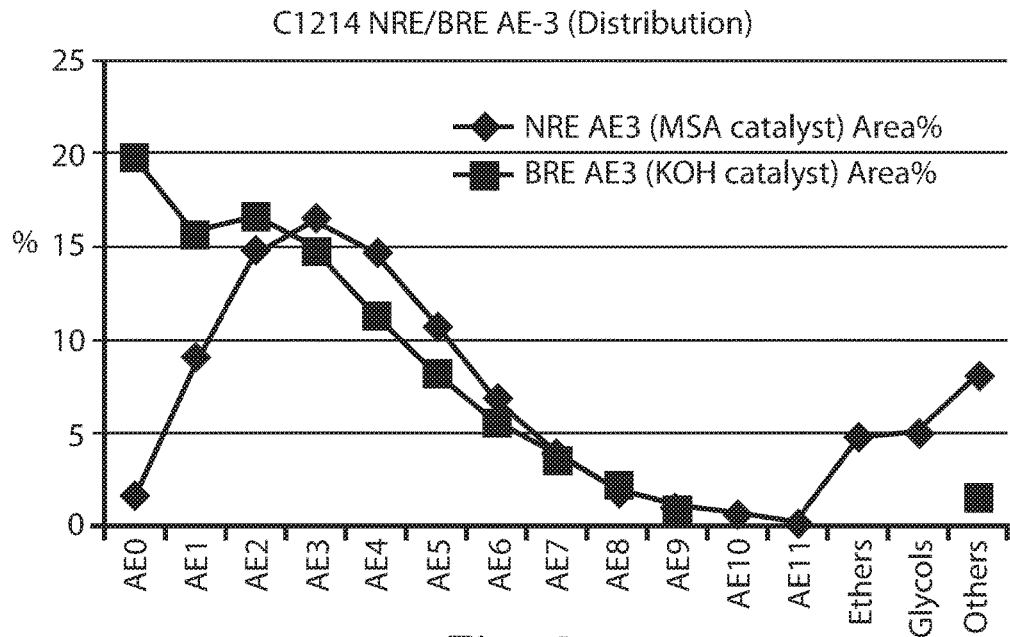
FIG. 3 illustrates the homolog distribution of ethoxylated $C_{12-14}$ alcohol prepared from the methane sulfonic acid (MSA)-catalyzed ethoxylation of the alcohol with 3 moles of ethylene oxide and the homolog distribution of ethoxylated $C_{12-14}$ alcohol prepared from the potassium hydroxide-catalyzed ethoxylation of the alcohol with 3 moles of ethylene oxide. The distribution is determined by GC.
Figure 4:
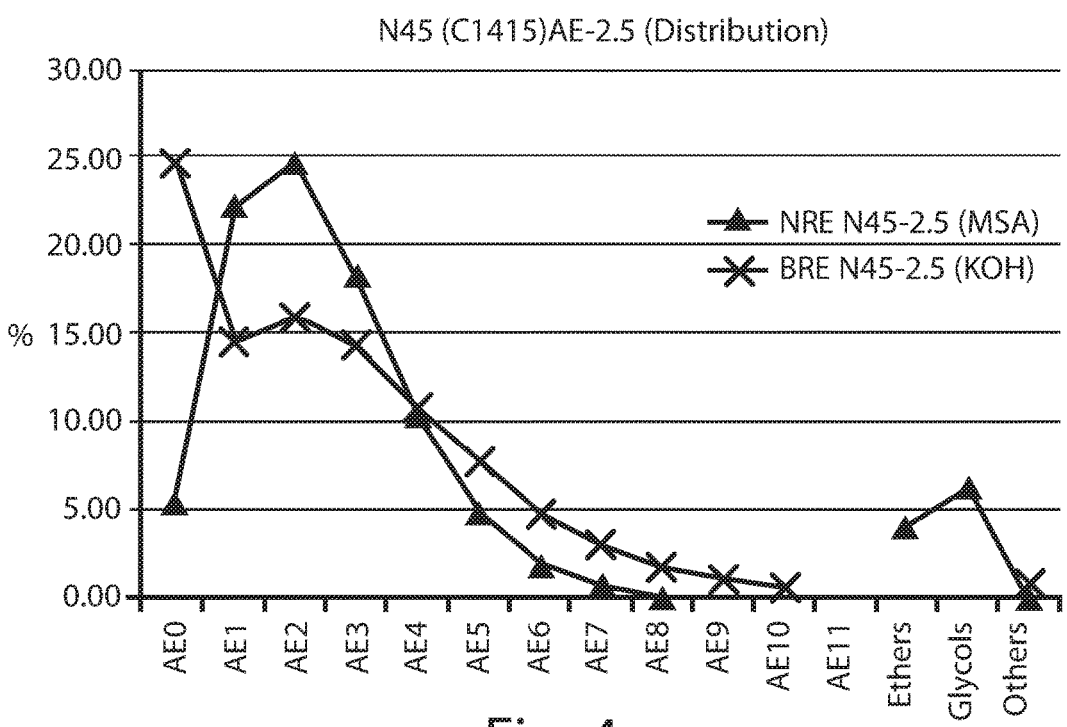
FIG. 4 illustrates the homolog distribution of ethoxylated $C_{14-15}$ alcohol prepared from the methane sulfonic acid (MSA)-catalyzed ethoxylation of the alcohol with 2.5 moles of ethylene oxide and the homolog distribution of ethoxylated $C_{14-15}$ alcohol prepared from the potassium hydroxide-catalyzed ethoxylation of the alcohol with 2.5 moles of ethylene oxide. The distribution is determined by GC.

As an example, FIGS. 1, 2, and 3 illustrate the homolog distribution of ethoxylated $C_{12-14}$ alcohol prepared from the conventional potassium hydroxide-catalyzed ethoxylation of the alcohol with 1, 2, and 3 moles of ethylene oxide, respectively. As shown in FIGS. 1, 2, and 3, the resulting ethoxylated product is not a single compound containing 1, 2, or 3 ($CH_2CH_2O$) units as the general formula (formula I, with n=1, 2, or 3) may suggest. Instead, the product is a mixture of several homologs whose total ethylene oxide units vary from 1 to 10. In contrast, FIGS. 1, 2, and 3 also illustrate the homolog distribution of ethoxylated $C_{12-14}$ alcohol prepared from the MSA-catalyzed ethoxylation of the alcohol with 1, 2, and 3 moles of ethylene oxide, respectively. In FIGS. 1, 2, and 3, the peaked distribution of the homologs is indicated by their higher concentration (weight %) at the target average degree of ethoxylation, e.g., for a target average degree of ethoxylation of 1, higher concentration of AE1 and AE2, for a target average degree of ethoxylation of 2, higher concentration of AE1, AE2, and AE3, for a target average degree of ethoxylation of 3, higher concentration of AE2, AE3, and AE4.

A "narrow range" or "peaked" alkoxylated alcohol composition may be desirable for a selected application. Homologs in the selected target distribution range may have the proper liphophilic-hydrophilic balance for a selected application. For example, in the case of an ethoxylated alcohol product comprising an average ratio of 3 ethylene oxide (EO) units per molecule, homologs having a desired lipophilic-hydrophilic balance may range from 2E0 to 4E0. Homologs with shorter EO chain length (<2EO) or longer EO chain length (>4EO) may not be desirable for the applications for which a 3 EO/alcohol ratio surfactant is ordinarily selected, since such longer and shorter homologs are either too lipophilic or too hydrophilic for the applications utilizing this product. Therefore, it is advantageous to develop an alkoxylated alcohol having a peaked distribution.

The narrow range alkoxylated alcohol compositions of the disclosure may have an average degree of ethoxylation ranging from about 0 to about 10. The narrow range alkoxylated alcohol compositions of the disclosure may have an average degree of ethoxylation ranging from about 1 to about 3. The narrow range alkoxylated alcohol compositions of the disclosure may have an average degree of ethoxylation of 1. The narrow range alkoxylated alcohol compositions of the disclosure may have an average degree of ethoxylation of 2. The narrow range alkoxylated alcohol compositions of the disclosure may have an average degree of ethoxylation of 3.

The compositions of the disclosure may comprise an alcohol ethoxylate of formula (I):

(I)

where R is selected from a saturated or unsaturated, linear or branched, $C_8$-$C_{20}$ alkyl group, where $0 \leq n \leq 10$, and where the average value of n is about 1, where less than about 7% by weight of the alcohol ethoxylate are ethoxylates having $n \geq 3$ and less than about 35% by weight of the alcohol ethoxylate are ethoxylates having n=0 (free alcohol).

The compositions of the disclosure may comprise an alcohol ethoxylate of formula (I):

(I)

where R is selected from a saturated or unsaturated, linear or branched, $C_8$-$C_{20}$ alkyl group, where $0 \leq n \leq 10$, and where the average value of n is about 2, where from about 9% to about 13%, or about 11%, by weight of the alcohol ethoxylate are ethoxylates having $n \geq 4$ and from about 9% to about 13%, or about 11%, by weight of the alcohol ethoxylate are ethoxylates having n=0 (free alcohol).

The compositions of the disclosure may comprise an alcohol ethoxylate of formula (I):

(I)

where R is selected from a saturated or unsaturated, linear or branched, $C_8$-$C_{20}$ alkyl group, where $0 \leq n \leq 10$, and where the average value of n is about 3, where from about 1% to about 5%, or about 3%, by weight of the alcohol ethoxylate are ethoxylates having n=0 (free alcohol).

The present disclosure also relates to derivatives of narrow range alcohol alkoxylates. There are a number of suitable derivatives of narrow range alcohol alkoxylates, such as sulfates, known as alcohol ethoxy sulfates. The narrow range molar distribution of the alcohol ethoxylate is maintained in the various derivatives, such as the alcohol ethoxy sulfate. Various processes of sulfating are well known in the art.

The alcohol ethoxylate and its derivatives, e.g., alcohol ethoxy sulfate, may be derived from a natural alcohol, a synthetic alcohol, or a mixture thereof.

The compositions described herein may further comprise (in addition to the alcohol ethoxylate or its sulfated derivative) residual alkoxylation catalyst, which may be considered residue from the reaction or an impurity. The alkoxylation catalyst may be selected from $C_{1-14}$ sulfonic acids. The alkoxylation catalyst may be selected from the group consisting of methane sulfonic acid, dodecylbenzene sulfonic acid, and mixtures thereof. $C_{1-14}$ sulfonic acids, particularly methane sulfonic acid and dodecylbenzene sulfonic acid, are common components of various cleaning products and detergents. For example, dodecylbenzene sulfonic acid is a "workhorse surfactant" in laundry detergent and methane sulfonic acid is used in beauty care compositions. As such, these catalysts need not be removed from alcohol ethoxylate product streams, thus simplifying the production process.

The composition(s) of the disclosure may further comprise from about 1% to about 10%, or from about 1% to about 6%, or about 3%, by weight of the composition of a catalyst selected from $C_{1-14}$ sulfonic acids. The composition(s) of the disclosure may comprise from about 1% to about 10%, or from about 1% to about 6%, or about 3%, by weight of the composition of a catalyst selected from the group consisting of methane sulfonic acid, dodecylbenzene sulfonic acid (DDBSA), and mixtures thereof. The composition(s) of the disclosure may comprise from about 1% to about 2% by weight of the composition of methane sulfonic acid. The composition(s) of the disclosure may comprise from about from about 2% to about 6% by weight of the composition of dodecyl benzene sulfonic acid.

The composition(s) of the disclosure may further comprise (in addition to the alcohol ethoxylate or its sulfated derivative) various impurities or by-products of the alkoxylation reaction. The impurities may vary depending on the catalyst used and the conditions of the reaction. Impurities include alkyl ethers, e.g., dialkyl ethers, such as, didodecyl ether, glycols, e.g., diethylene glycol, triethylene glycol, pentaethylene glycol, other polyethylene glycols, ethoxylated sulfonates (when DDBSA is used as catalyst).

By using the alkoxylation catalysts described herein, the amount of the impurities produced during the alkoxylation reaction and during subsequent sulfation reaction(s) may be reduced, particularly as compared to known alkoxylation catalysts that produce narrow range alkoxylates. Impurities that may be produced during a subsequent sulfation reaction(s) include 1,4-dioxane, a cyclic diether.

The composition(s) of the disclosure may comprise from about 0.01% to about 4%, or about 0.1% to about 4%, or about 1% to about 4%, by weight of the composition of an impurity selected from the group consisting of alkyl ether, glycol, and ethoxylated sulfonates.

The composition(s) of the disclosure may comprise from about 1% to about 10%, or from about 1% to about 6%, or about 3%, by weight of the composition of a catalyst selected from $C_{1-14}$ sulfonic acids and/or from about 0.1% to about 4% by weight of the composition of an impurity selected from the group consisting of alkyl ether, glycol, and ethoxylated sulfonates. The composition(s) of the disclosure may comprise from about 1% to about 2% by weight of the composition of methane sulfonic acid and/or from about 0.1% to about 2% by weight of the composition of alkyl ether (as an impurity). The composition(s) of the disclosure may comprise from about 2% to about 6% by weight of the composition of dodecyl benzene sulfonic acid and/or from about 0.1% to about 4% by weight of the composition of an impurity selected from the group consisting of alkyl ethers, glycols, and ethoxylated sulfonates.

The present disclosure further encompasses concentrated compositions, often referred to as pastes, which may be combined with various adjunct ingredients and water to make a variety of detergent products, including liquid laundry detergent. The present disclosure relates to a concentrated composition comprising from about 1% to about 10%, or from about 1% to about 6%, or about 3%, by weight of the composition of a $C_{1-14}$ sulfonic acid, e.g., methane sulfonic acid, dodecylbenzene sulfonic acid, and from about 50% to about 99%, or from about 70% to about 99%, by weight of a narrow range alcohol ethoxylate having an average degree of ethoxylation ranging from about 1 to about 10. The present disclosure further relates to a concentrated composition comprising from about 1% to about 10%, or from about 1% to about 6%, or about 3%, by weight of the composition of a $C_{1-14}$ sulfonic acid, e.g., methane sulfonic acid, dodecylbenzene sulfonic acid, and from about 10% to about 85%, or from about 30% to about 70%, by weight of a narrow range alcohol ethoxy sulfate having an average degree of ethoxylation ranging from about 1 to about 10.

Catalyst and Process of Making Narrow Range Alcohol Alkoxylates

The alkoxylation catalysts described herein allow for the preparation of alcohol alkoxylates having a narrow distribution of alkylene oxide addition moles. It is believed that, in a conventional base-catalyzed alkoxylation reaction, for example, a KOH-catalyzed alcohol ethoxylation reaction, there is a tendency for ethylene oxide to react with alcohol ethoxylate conjugates (alcohol ethoxylate conjugates are more acidic), rather than to react with unreacted alcohol conjugates, thereby yielding a broad range distribution having greater percentages of free alcohol and high-degree ethoxylated alcohols. High-degree ethoxylated alcohols are believed to contribute to the increased production of 1,4-dioxane (an undesirable by-product), when such high-degree ethoxylated alcohols are sulfated to produce alcohol ethoxy sulfates. In an acid-catalyzed alkoxylation reaction, such as that of the present invention, no alcohol or alcohol ethoxylate conjugates are present and the reaction products are driven by the probability of an ethylene oxide initiator attacking an alcohol molecule or an alcohol ethoxylate molecule.

The alkoxylation catalysts described herein have a number of advantages for commercial manufacturing compared with known catalysts that provide narrow distribution alkoxylates. The alkoxylation catalysts described herein comprise conventionally used, low-cost raw materials, and the catalysts may be readily prepared. The alkoxylation catalysts described herein are also stable and, therefore, readily handled. Also, the reaction rate, using the alkoxylation catalysts described herein, is similar to previously used alkaline catalysts and suitable for commercial production.

The alkoxylation catalysts described herein are suitable for alkoxylating natural or synthetic, linear or branched, saturated or unsaturated, $C_{8-20}$ alcohols, alkyl phenols, polyols, etc. having 4-22 carbon atoms. Suitable alcohols include pure linear materials (naturals), lightly branched in $C_2$ position (Neodols®), lightly random-branched (Safols®), highly branched in $C_2$ position (Isalchem®), and highly branched mid-chain materials (HSA). Suitable synthetic alcohols include those sold by Shell Chemical Company under the trademark Neodol®, including Neodol® 25, Neodol® 23, and Neodol® 45. Suitable natural alcohols include $C_{12-14}$. In addition, known reaction procedures, reaction conditions, and reactors for alkylene oxides may be used with the alkoxylation catalyst described herein.

The alkoxylation processes described herein may also be run in a series, initially using the acid catalyst described herein and then using a conventional, known catalyst, such as KOH, to yield alkoxylates having a distribution of alkylene oxide addition moles that is narrower than that produced by KOH catalyst alone but broader than that produced by the catalysts of the invention alone. Running the alkoxylation process in series may be particularly useful for higher ethoxylation degree targets, e.g., EO4, EO5, EO6.

The alkoxylation reaction itself may be performed in a single pot or in a continuous process. The ethylene oxide (EO) may initially be reacted with the catalyst, which activates EO to nucleophilic attack. Continuous plant processes with suitable residence time may be used.

The alkoxylation processes disclosed herein may be used to produce alcohol ethoxylates of varying degrees of ethoxylation, including the EO1, EO2, and EO3 targets that are specifically called out. The alkoxylation processes disclosed herein may be also be used to produce other alcohol alkoxylates, e.g., propoxylated alcohol, of varying degress of alkoxylation.

A suitable method for preparing an ethoxylated alcohol as disclosed herein includes the steps of: i) reacting an excess (for example, from about 0% to about 5% excess) of ethylene oxide with a linear or branched, $C_{8-20}$ alcohol for stoichiometric target mole ratio of ethylene oxide, in the presence of about 1% to about 10% of a catalyst selected from $C_{1-14}$ sulfonic acids, or selected from the group consisting of methane sulfonic acid, dodecylbenzene sulfonic acid (DDBSA), and mixtures thereof, in an ethoxylation vessel with an appropriate heat removal mechanism, for example, recirculating via an external heat exchanger or using a coil or jacket system; ii) optionally, separating at least a portion of the unreacted, linear or branched, $C_{8-20}$ alcohol from the product of step i) and iii) recycling the unreacted linear or branched, $C_{8-20}$ alcohol back into the ethoxylation vessel; (iv) post-treating the product via neutralizing and followed by peroxide treatment under vacuum and stripping with steam to remove dioxane formed during the reaction.

The present disclosure relates to a process for preparing a narrow range alcohol ethoxylate comprising the steps of: i) reacting ethylene oxide with a linear or branched, $C_{8-20}$ alcohol in the presence of about 1% to about 10% of a catalyst selected from $C_{1-14}$ sulfonic acids; ii) post-treating the product of step i).

The present disclosure relates a process for preparing a narrow range alcohol ethoxylate comprising the steps of: i) reacting ethylene oxide with a linear or branched, $C_{8-20}$ alcohol in the presence of about 1% to about 10% of a catalyst selected from $C_{1-14}$ sulfonic acids; ii) reacting the product of step i) with a basic catalyst; iii) post-treating the product of step ii).

Applications and Uses

Narrow range alkoxylated alcohols are desirable in a number of applications, particularly in surfactant applications. Narrow range alkoxylate alcohols may be used directly as nonionic surfactants or sulfated to produce anionic surfactants, namely alcohol ethoxy sulfates. Both types of surfactants have numerous uses, including in cleaning compositions or detergents, e.g., laundry detergents.

The narrow range alkoxylated alcohols of the disclosure and the derivatives thereof may be used in detergents at various concentrations. Such detergents may also contain adjuncts. Suitable adjuncts may be selected from the group consisting of a builder, an organic polymeric compound, an enzyme, an enzyme stabilizer, a bleach system, a brightener, a hueing agent, a chelating agent, a suds suppressor, a conditioning agent, a humectant, a perfume, a filler or carrier, an alkalinity system, a pH control system, and a buffer, and mixtures thereof.

EXAMPLES

AE1 Examples

Example 1 (MSA Catalyst—Small Scale Reactor-T422)

A small lab scale batch reactor is used for the trial. 11 gm $C_{12}$-alcohol is taken in the reactor vessel and heated to the reaction temperature of 180 degree C. The reactor stirrer is set to 1500 RPM. 1 wt % (of alcohol) Methane Sulfonic Acid (MSA) catalyst amount is added to the reactor. The reactor vessel is sealed and the mixture is purged with $N_2$ gas two times. In the final purging, the reactor vessel is left with 1 barg $N_2$ pressure. At the reaction temperature of 180 degree C., 2.9 gm of ethylene oxide is introduced inside the reactor using a dosing pipe with a nitrogen line to provide overhead pressure. The reaction is carried out for three hours after ethylene oxide insertion into the reactor vessel and then product is cooled and purged with nitrogen before collecting for analysis.

Example 2 (DDBSA Catalyst—Small Scale Reactor-T325)

A small lab scale batch reactor is used for the trial. 11 gm $C_{12}$-alcohol is taken in the reactor vessel and heated to the reaction temperature of 160 degree C. The reactor stirrer is set to 1500 RPM. 4 wt % (of alcohol) Dodecyl benzene Sulfonic Acid (DDBSA) catalyst amount is added to the reactor. The reactor vessel is sealed and the mixture is purged with $N_2$ gas two times. In the final purging, the reactor vessel is left with 1 barg $N_2$ pressure. At the reaction temperature of 160 degree C., 3.4 gm of ethylene oxide is introduced inside the reactor using a dosing pipe with the help of a nitrogen line overhead pressure. The reaction is carried out for two hours after ethylene oxide insertion into the reactor vessel and then product is cooled and purged with nitrogen before collecting for analysis.

Example 3 (MSA Catalyst—Pilot Scale Jet Loop Reactor-T500)

A pilot scale jet loop reactor is used for the trial. 21.4632 Kg of $C_{12-14}$ alcohol feedstock is transferred in the reactor using a vacuum and the reactor is purged with $N_2$ gas. The heater is set to the reaction temperature of 160 degree C. and the recirculation pump is then turned on. When the feedstock alcohol temperature reaches around 150 degree C., the circulation pump is turned off and the 433.6 gm catalyst mixture (216.8 gm of MSA catalyst premixed with 216.8 gm of alcohol) is introduced into the reactor using a vacuum. The reactor is purged with $N_2$ three times. In the final purging, the reactor vessel is left with 0.6 barg $N_2$ pressure. The recirculation pump is turned on. Once the temperature reaches a set reaction temperature of 160 degree C., the ethylene oxide is introduced into the reactor by opening the inlet valve to bring up the pressure in the reactor to about 5 barg. Then EO is added periodically to maintain the pressure in the reactor at around 5 barg throughout the reaction process. Once a total of 4.88 kg EO is inserted into the reactor (in approximately 8 hr 20 mins), the reaction is finished. Thereafter, 30 minutes are given for the product to cook out in the reactor at the reaction temperature. The product is then cooled to about 60 degree C. and collected for analysis after purging off the remaining gases from the reactor using $N_2$. From the recirculation line, intermediary samples are taken periodically and analyzed to monitor the reaction progress.

Example 4 (DDBSA Catalyst—Pilot Scale Jet Loop Reactor-T504)

A pilot scale jet loop reactor is used for the trial. 20.8128 Kg of $C_{12-14}$ alcohol feedstock is transferred in the reactor using a vacuum and the reactor is purged with $N_2$ gas. The heater is set to the reaction temperature of 160 degree C. and the recirculation pump is then turned on. When the feedstock alcohol temperature reaches around 150 degree C., the circulation pump is turned off and 1734.4 gm catalyst mixture (867.2 gm of DDBSA catalyst premixed with 867.2 gm of alcohol) is introduced into the reactor using a vacuum. The reactor is purged with $N_2$ three times. In the final purging, the reactor vessel is left with 0.2 barg $N_2$ pressure. The recirculation pump is turned on. Once the temperature reaches a set reaction temperature of 160 degree C., the ethylene oxide is introduced into the reactor by opening the inlet valve to bring up the pressure in the reactor to about 5 barg. Then EO is added periodically to maintain the pressure in the reactor at around 5 barg throughout the reaction process. Once a total of 4.88 kg EO is inserted into the reactor (in approximately 4 hr 30 mins), the reaction is finished. Thereafter, 30 minutes are given for the product to cook out in the reactor at the reaction temperature. The product is then cooled to about 60 degree C. and collected for analysis after purging off the remaining gases from the reactor using $N_2$. From the recirculation line, intermediary samples are taken periodically and analyzed to monitor the reaction progress.

AE2 Example

Example 5 (MSA Catalyst—Pilot Scale Jet Loop Reactor-T514)

A pilot scale jet loop reactor is used for the trial. 18.4132 Kg of $C_{12-14}$ alcohol feedstock is transferred in the reactor using a vacuum and the reactor is purged with $N_2$ gas. The heater is set to the reaction temperature of 160 degree C. and the recirculation pump is then turned on. When the feedstock alcohol temperature reaches around 150 degree C., the circulation pump is turned off and 433.6 gm of catalyst mixture (216.8 gm of MSA catalyst premixed with 216.8 gm of alcohol) is introduced into the reactor using a vacuum. The reactor is purged with $N_2$ three times. In the final purging, the reactor vessel is left with 0.4 barg $N_2$ pressure. The recirculation pump is turned on. Once the temperature reaches a set reaction temperature of 160 degree C., the ethylene oxide is introduced into the reactor by opening the inlet valve to bring up the pressure in the reactor to about 5 barg. Then EO is added periodically to maintain the pressure in the reactor at around 5 barg throughout the reaction process. Once a total of 4.2 kg EO is inserted into the reactor, the reaction is finished. The AE1 product is then cooled to about 80 degree C. and 216.8 gm product is collected after purging off the remaining gases from the reactor using $N_2$.

The collected AE1 product is mixed with another 216.8 gm of MSA catalyst. This new catalyst mixture is injected back into the reactor after the reactor product is heated back to 160 degree C. The reactor vessel is purged off with $N_2$ leaving final $N_2$ pressure to 0.4 barg in the final purging. Again, ethylene oxide is introduced into the reactor to continue the ethoxylation reaction. This is done in the same manner as in the AE1 production, maintaining the pressure at about 5 barg in the reactor. After an additional 4.2 Kg of EO is inserted into the reactor, the reaction is finished. Thereafter, 30 minutes are given for the product to cook out in the reactor at the reaction temperature. The AE2 product is then cooled to about 60 degree C. and collected for analysis after purging off the remaining gases from the reactor using $N_2$. From the recirculation line, intermediary samples are taken periodically and analyzed to monitor the reaction progress.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising from about 1% to about 10% by weight of the composition of a $C_{1-14}$ sulfonic acid and an alcohol ethoxylate of formula (I):

where R is selected from a saturated or unsaturated, linear or branched, $C_8$-$C_{20}$ alkyl group, where $0<n\leq 10$, and where the average value of n is about 1, where from about 9% to about 13% by weight of the alcohol ethoxylate are ethoxylates having $n\geq 4$ and from about 9% to about 13% by weight of the alcohol ethoxylate are free alcohol.

2. The composition of claim 1, wherein said alcohol ethoxylate is sulfated.

3. A detergent composition comprising the composition of claim 2 wherein said detergent composition is a form selected from the group consisting of a granular detergent, a bar-form detergent, a liquid laundry detergent, a gel detergent, a single-phase or multi-phase unit dose detergent, a detergent contained in a single-phase or multi-phase or multi-compartment water soluble pouch, a liquid hand dishwashing composition, a laundry pretreat product, a detergent contained on or in a porous substrate or nonwoven sheet, a automatic dishwashing detergent, a hard surface cleaner, a fabric softener composition, and mixtures thereof.

4. The composition of claim 1 comprising from about 1% to about 2% by weight of the composition of methane sulfonic acid and from about 0.1% to about 2% by weight of the composition of an alkyl ether.

5. The composition of claim 1 comprising from about 2% to about 6% by weight of the composition of dodecyl benzene sulfonic acid and from about 0.1% to about 4% by weight of the composition of an impurity selected from the group consisting of alkyl ethers, glycols, and ethoxylated sulfonates.

6. The composition of claim 1 wherein said alcohol ethoxylate is derived from a natural alcohol, a synthetic alcohol, or a mixture thereof.

7. A detergent composition comprising the composition of claim 1, wherein said detergent composition is a form selected from the group consisting of a granular detergent, a bar-form detergent, a liquid laundry detergent, a gel detergent, a single-phase or multi-phase unit dose detergent, a detergent contained in a single-phase or multi-phase or multi-compartment water soluble pouch, a liquid hand dishwashing composition, a laundry pretreat product, a detergent contained on or in a porous substrate or nonwoven sheet, a automatic dishwashing detergent, a hard surface cleaner, a fabric softener composition, and mixtures thereof.

* * * * *